(12) United States Patent
Tajima et al.

(10) Patent No.: US 8,874,349 B2
(45) Date of Patent: Oct. 28, 2014

(54) SENSOR CONTROL APPARATUS AND SENSOR CONTROL METHOD

(75) Inventors: Tomohiro Tajima, Kasugai (JP); Satoshi Ishikawa, Kani (JP); Kunihiko Yonezu, Inabe (JP)

(73) Assignee: NGK Spark Plug Co., Ltd., Aichi (JP)

( * ) Notice: Subject to any disclaimer, the term of this patent is extended or adjusted under 35 U.S.C. 154(b) by 449 days.

(21) Appl. No.: 13/419,804

(22) Filed: Mar. 14, 2012

(65) Prior Publication Data

US 2012/0239271 A1 Sep. 20, 2012

(30) Foreign Application Priority Data

Mar. 14, 2011 (JP) ................................ 2011-055602

(51) Int. Cl.

| F02D 28/00 | (2006.01) |
| B60W 10/06 | (2006.01) |
| F02D 41/14 | (2006.01) |
| F02N 11/08 | (2006.01) |
| F02D 41/04 | (2006.01) |
| G01N 33/18 | (2006.01) |

(52) U.S. Cl.
CPC ........ F02N 11/0814 (2013.01); F02D 41/1494 (2013.01); F02D 41/042 (2013.01); G01N 33/18 (2013.01); G01N 33/1826 (2013.01); F02D 41/1455 (2013.01); Y02T 10/48 (2013.01)
USPC ......... 701/102; 701/110; 701/114; 123/198 D

(58) Field of Classification Search
CPC . B06F 10/06; F02D 41/1405; F02D 41/1456; F02D 41/042; F02D 41/222; F02D 11/105

USPC ................. 701/102, 106, 109, 110, 112, 114; 123/179.4, 179.12, 198 D, 198 DB, 123/198 DC, 198 F, 692–694, 696; 204/424, 204/431, 432

See application file for complete search history.

(56) References Cited

U.S. PATENT DOCUMENTS

| 5,535,614 | A | * | 7/1996 | Okamoto et al. ............ 73/23.31 |
| 6,068,746 | A | | 5/2000 | Kojima et al. |
| 7,360,395 | B2 | * | 4/2008 | Sasaki et al. ................ 73/25.05 |
| 7,418,855 | B2 | * | 9/2008 | Oishi et al. .................. 73/25.03 |
| 7,743,759 | B2 | * | 6/2010 | Aoki ............................ 123/672 |
| 8,594,908 | B2 | * | 11/2013 | Yoshikawa et al. ........... 701/108 |

(Continued)

FOREIGN PATENT DOCUMENTS

| JP | 10132779 A | 5/1998 |
| JP | 2003148206 A | 5/2003 |

Primary Examiner — Stephen K Cronin
Assistant Examiner — Johnny H Hoang
(74) Attorney, Agent, or Firm — Sughrue Mion, PLLC

(57) ABSTRACT

A sensor control apparatus including a gas sensor having a sensor element, a housing and a base part formed of a resin. The apparatus includes a heating part and a control part. When the control part determines that a predetermined automatic stop condition has been satisfied, the control part switches from a control for maintaining the temperature of the sensor element at an activating temperature to a control in a stop state for reducing at least one of voltage and current supplied to the heating part so as to set a temperature of the base part to a value equal to or lower than a shape holding temperature of the resin. Also disclosed is a sensor control method for holding a temperature of a sensor element to an activating temperature.

10 Claims, 7 Drawing Sheets

(56) References Cited

U.S. PATENT DOCUMENTS

| | | | |
|---|---|---|---|
| 2007/0125348 A1* | 6/2007 | Aoki | 123/676 |
| 2007/0156322 A1* | 7/2007 | Soga et al. | 701/104 |
| 2007/0204840 A1* | 9/2007 | Abe | 123/697 |
| 2009/0173327 A1* | 7/2009 | Aoki | 123/693 |

* cited by examiner

SENSOR CONTROL APPARATUS AND SENSOR CONTROL METHOD

BACKGROUND OF THE INVENTION

1. Field of the Invention

The present invention relates to a sensor control apparatus and a sensor control method, each of which is suitable for application to a sensor used for controlling an internal combustion engine, in particular, a gas sensor for measuring a concentration of the particular gas component.

2. Description of the Related Art

In general, in an internal combustion engine used as the driving source of a movable body such as a vehicle, a control for optimizing a combustion parameter in the engine has come into wide use in order to improve an output power or a fuel cost or purify exhaust gas, for example. As the combustion parameter, there is an air-fuel ratio which is obtained by dividing an air mass in a mixture of the air and fuel burnt in the engine by a fuel mass. The air-fuel ratio is controlled so as to be a value suitable for an operation state of the engine, for example, a theoretical air-fuel ratio for combusting the air and fuel in just proportion or a predetermined value near the theoretical air-fuel ratio.

In the case of actually performing the aforesaid control, an accurate estimate of the air mass in the air-fuel ratio, more concretely, the oxygen mass is needed. Accordingly, a technique has been developed in which an air flow sensor for measuring the flow rate of the air sucked into the engine and an oxygen sensor for measuring the concentration of oxygen gas remaining in burned exhaust gas, for example, are provided to more accurately obtain an air-fuel ratio (see, for example, Patent Literature 1).

In the aforesaid oxygen sensor, in general, the measurement accuracy of oxygen concentration depends on the temperature of a sensor element as a measuring part. Thus, the oxygen sensor is provided with a heater, etc., for controlling the temperature of the sensor element in a predetermined range. Further, in a related art oxygen sensor, a base part, protruding outside of a flow path of the exhaust gas at the time of being attached to the engine, is configured by assembling plural members each formed by processing a thin metal plate. However, according to the method of configuring the base part using the thin metal plate, problems have been encountered in that the structure becomes complicated and the assembly procedure is troublesome.

In view of the above, a technique has been proposed in which the base part of the oxygen sensor is configured by a resin member which can be processed easier than the metal thin plate (see Patent Literature 2). Since the base part is configured by the resin member capable of forming a complicated shape, the number of components constituting the base part can be reduced, whereby the structure can be simplified and the procedure for assembly is unnecessary.

[Patent Literature 1] JP-A-10-132779
[Patent Literature 2] JP-A-2003-148206

3. Problems to be Solved by the Invention

On the other hand, in recent years, in order to reduce an amount of carbon dioxide exhausted from an internal combustion engine or to reduce fuel cost, an idling stop control has come into use. In the idling stop control, the engine is automatically stopped when a predetermined condition is satisfied such that a vehicle, etc., is stopped, and thereafter the engine is automatically started again when a driver operates to start the vehicle, etc. When the engine is automatically stopped (idling stop) by the idling stop control, since the suction of air and exhaust of the exhaust gas in the engine is also stopped, the flow of gas around the oxygen sensor also stops.

As a result, an amount of heat drawn into the ambient gas from the sensor element and a metal housing, etc., is reduced. Then, when the temperature of the sensor element heated by the heater so as to be kept at an activating temperature is maintained, the temperature of the main body of the oxygen sensor such as the housing for housing the sensor element is apt to increase. Like the oxygen sensor described in Patent Literature 2, in a sensor in which a portion above a housing is configured by a resin member having lower degree of thermal resistance than that of a metal material, a problem arises that, in the idling stop state, the resin member constituting the oxygen sensor is influenced by heat transmitted from the sensor element and hence the temperature of the resin member may exceed its heat proof temperature.

SUMMARY OF THE INVENTION

This invention has been made in order to solve the aforesaid problem, and an object thereof is to provide a sensor control apparatus and a sensor control method, each of which is used for an internal combustion engine where an idling stop control is performed, and which can suppress the temperature of a gas sensor, having a resin member and measuring the concentration of the particular gas component, to a value equal to or lower than the heat proof temperature of the resin.

The above object of the invention has been achieved by providing, in a first aspect (1), a sensor control apparatus comprising: a gas sensor which comprises, a sensor element for measuring a concentration of a particular gas component contained in a gas flowing within a pipe disposed in an internal combustion engine, a housing which houses the sensor element therein and is inserted into the pipe, and a base part which is formed of a resin, attached to the housing and disposed on an outer side of the pipe; a heating part which increases a temperature of the sensor element; and a control part which adjusts at least one of voltage and current supplied to the heating part to maintain the temperature of the sensor element at an activating temperature, wherein the control part determines whether or not, when the internal combustion engine having been driven is stopped, the internal combustion engine is stopped in a manner satisfying a predetermined automatic stop condition, and wherein when it is determined that the internal combustion engine is stopped in the manner satisfying the predetermined automatic stop condition, the control part switches from a control for maintaining the temperature of the sensor element at the activating temperature to a control in a stop state for reducing at least one of the voltage and current supplied to the heating part to thereby set a temperature of the base part to a value equal to or lower than a shape holding temperature of the resin.

According to the sensor control apparatus of the invention, when the engine stops in the manner of satisfying the predetermined automatic stop condition, in other words, when the engine stops by the idling stop control, the control part starts the control in the stop state for reducing at least one of the voltage and current supplied to the heating part. An amount of the reduction of at least one of the voltage and current is set to an amount which can reduce an amount of heat transmitted to the base part from the sensor element to thereby set the temperature of the base part to a value equal to or lower than the shape holding temperature of the resin, in the case where the engine stops. That is, when the flow of gas flowing through the pipe stops, an amount of heat drawn from the sensor element by the gas is reduced.

The activating temperature is a temperature necessary for the sensor element to measure the concentration of the particular gas component. The activating temperature differs depending on the material used for the sensor element. For example, in the case of a sensor element for measuring the oxygen concentration using zirconia ($ZrO_2$), the activating temperature is a temperature necessary for zirconia to act as oxygen ion conductor.

The shape holding temperature of the resin is a temperature that can maintain the shape of the base part formed of a resin so as to be able to attain the function of the base part. For example, the shape holding temperature of the resin is a temperature determined based on a deflection temperature under load of the resin to be used, a melting point of the resin to be used, etc., thereof as a parameter. Since the temperature as an index of the temperature capable of maintaining the shape differs depending on the kind of resin used for the base part, it is preferable to select a suitable temperature from plural temperatures such as the deflection temperature under load according to the resin to be used. For example, polyphenylene sulfide, polybutylene terephthalate and polyethylene sulfide can be used as the resin for forming the base part, and when one of these resins is used, the deflection temperature under load can be set as the parameter.

In a preferred embodiment (2) according to the sensor control apparatus (1), the control part can perform the control of stopping the supply of electric power to the heating part at the time of performing the control in a stop state. However, it is preferable to continue the supply of electric power to the heating part even at the time of performing the control in a stop state.

Since the heating part is continuously supplied with the electric power, when the driving of the engine having been stopped by the idling stop control is started again, the temperature of the sensor element can be quickly increased (restored) to the activating temperature within a time period not adversely affecting the control (air-fuel ratio control, for example) of the engine In another preferred embodiment (3) according to (1) or (2) above, at the time of performing the control in a stop state, the control part adjusts at least one of the voltage and current supplied to the heating part so that the temperature of the sensor element becomes 100° C. or higher and lower than the activating temperature.

In this manner, since the temperature of the sensor element is kept to 100° C. or higher and lower than the activating temperature at the time of performing the control in a stop state, even when the engine is stopped by the idling stop control and the control of reducing the temperature of the sensor element is performed, the sensor element can be prevented from being adhered with water (water droplets contained in the exhaust gas). In other words, since the temperature of the sensor element is kept to be 100° C. or higher, the water is evaporated and does not adhere to the sensor element as soon as the water contacts the sensor element.

Thus, when the engine having been stopped by the idling stop control is driven again and the temperature of the sensor element is increased so as to reach the activating temperature, the following phenomenon can be suppressed. That is, the sensor element has a portion which is not adhered with water droplets and hence the heating process thereof is promoted. The sensor element also has another portion which is adhered with water droplets and hence the heating process thereof is delayed. Thus, the sensor element may be damaged by thermal shock caused by a sharp increase in temperature of the other portion when the water droplets adhered thereto evaporate.

In a preferred embodiment (4) according to (1) or (2) above, at the time of performing the control in a stop state, the control part adjusts at least one of the voltage and current supplied to the heating part so that the temperature of the sensor element becomes 300° C. or higher and lower than the activating temperature.

In this manner, since the temperature of the sensor element is kept to 300° C. or higher and lower than the activating temperature at the time of performing the control in a stop state, even when the engine is stopped by the idling stop control and the control of reducing the temperature of the sensor element is performed, the sensor element can be prevented from being adhered with oil. In other words, since the temperature of the sensor element is kept to 300° C. or higher, the oil is evaporated and does not adhere to the sensor element as soon as the oil contacts the sensor element. Thus the adhering of soot due to adherence of oil to the sensor element can be suppressed.

In preferred embodiment (5) according to (1) or (2) above, at the time of performing the control in a stop state, the control part adjusts at least one of the voltage and current supplied to the heating part so that the temperature of the sensor element becomes 600° C. or higher and lower than the activating temperature.

In this manner, since the temperature of the sensor element is kept to 600° C. or higher and lower than the activating temperature at the time of performing the control in a stop state, even when the engine is stopped by the idling stop control and the control of reducing the temperature of the sensor element is performed, the sensor element can be prevented from being adhered with soot in addition to oil. In other words, since the temperature of the sensor element is kept to 600° C. or higher, the soot thus adhered is burnt and hence does not remain on the sensor element even if the soot initially is adhered to the sensor element. Thus, the output according to the concentration of the particular gas can be suppressed from being influenced by conductive soot attached to and remaining on the sensor element.

In a preferred embodiment (6) according to any of (1) to (5) above, the control part switches to control in a stop state upon a lapse of a predetermined time period after it is determined that the internal combustion engine is stopped due to satisfaction of the predetermined automatic stop condition.

Immediately after the stop of the engine due to satisfaction of the predetermined automatic stop condition, the temperature of the base part does not promptly exceed the shape holding temperature of the resin even when the control part continues the control of holding the temperature of the sensor element to the activating temperature by using the heating part. Thus, in this invention, the control part switches into the control in a stop state upon the lapse of the predetermined time period after it is determined that the engine is stopped due to satisfaction of the predetermined automatic stop condition. Accordingly, when the engine is driven again immediately after it is determined that the engine is stopped due to satisfaction of the predetermined automatic stop condition, since the temperature of the sensor element is not reduced and maintains the activating temperature, the control (air-fuel ratio control, for example) of the engine can be continued favorably. The predetermined time period is a time period during which the temperature of the base part is maintained to a temperature lower than the shape holding temperature of the resin in the case where the control for holding the temperature of the sensor element to the activating temperature using the heating part is continued, after the predetermined automatic stop condition is satisfied.

In a preferred embodiment (7) according to any of (1) to (6) above, the control part controls electric energy supplied to the heating part so as to be constant, when the control in a stop state.

According to such an arrangement, the control for setting the temperature of the base part so as to be equal to or lower than the shape holding temperature of the resin can be realized by the simple control of setting the electric energy supplied to the heating part to a constant amount.

In a preferred embodiment (8) according to any of (1) to (6) above, while the internal combustion engine is driven, the control part adjusts at least one of the voltage and current supplied to the heating part so as to attain an element resistance value of the sensor element corresponding to the activating temperature, and wherein at the time of performing the control in a stop state, the control part adjusts at least one of the voltage and current supplied to the heating part so as to attain an element resistance value corresponding to a temperature of the sensor element at which a temperature of the base part is equal to or lower than the shape holding temperature of the resin.

In this manner, since the voltage and current supplied to the heating part is adjusted so as to attain the element resistance value of the sensor element which changes according to the temperature of the sensor element, the temperature of the sensor element during the control in a stop state can be made almost constant. Consequently, the temperature of the base part during the control in a stop state can be surely controlled to a temperature equal to or lower than the shape holding temperature of the resin.

In a preferred embodiment (9) according to any of (1) to (8) above, the housing is provided with a seal part which closes a gap between the housing and the pipe to thereby prevent the gas from flowing outside of the pipe.

Since the housing is provided with the seal part which closes the gap between the housing and the pipe, the gas can be prevented from flowing outside of the pipe. The seal part is preferably formed by resin having elasticity in a view point of preventing gas leakage. Even in the case where the seal part is formed by a resin having elasticity, since the control part performs the control in a stop state, the seal part can be suppressed from being damaged such as by softening due to the temperature increase of the seal part.

In accordance with a second aspect (10), the present invention provides a sensor control method for holding a temperature of a sensor element at an activating temperature using a heating part for heating the sensor element, in a gas sensor which comprises the sensor element for measuring a concentration of a particular gas component contained in a gas flowing within a pipe disposed in an internal combustion engine, a housing which houses the sensor element therein and is inserted into the pipe, and a base part which is formed of a resin, attached to the housing and disposed on an outer side of the pipe, the method comprising a determining step of determining whether or not, when the internal combustion engine having been driven is stopped, the internal combustion engine is stopped in a manner satisfying a predetermined automatic stop condition; and when it is determined that the internal combustion engine is stopped in the manner satisfying the predetermined automatic stop condition, a control step of stopping a control for maintaining the temperature of the sensor element at the activating temperature and starting a control in a stop state for reducing at least one of voltage and current supplied to the heating part to thereby set a temperature of the base part to a value equal to or lower than a shape holding temperature of the resin.

According to the sensor control method of this invention, when the engine stops in the manner of satisfying the predetermined automatic stop condition, the control in the stop state for reducing at least one of the voltage and current supplied to the heating part is started. Thus, the temperature of the sensor element during the control in a stop state can be reduced and the temperature of the base part can be held to a value equal to or lower than the shape holding temperature of the resin.

Effects of the Invention

According to the sensor control apparatus and the sensor control method of the invention, when the engine stops in the manner of satisfying the predetermined automatic stop condition, the control part performs the control in the stop state for reducing at least one of the voltage and current supplied to the heating part. Thus, the temperature of the sensor element can be reduced and the temperature of the base part can be suppressed to a temperature equal to or lower than the shape holding temperature of the resin, that is, the heat proof temperature thereof.

REFERENCE NUMERALS

Figure 1:
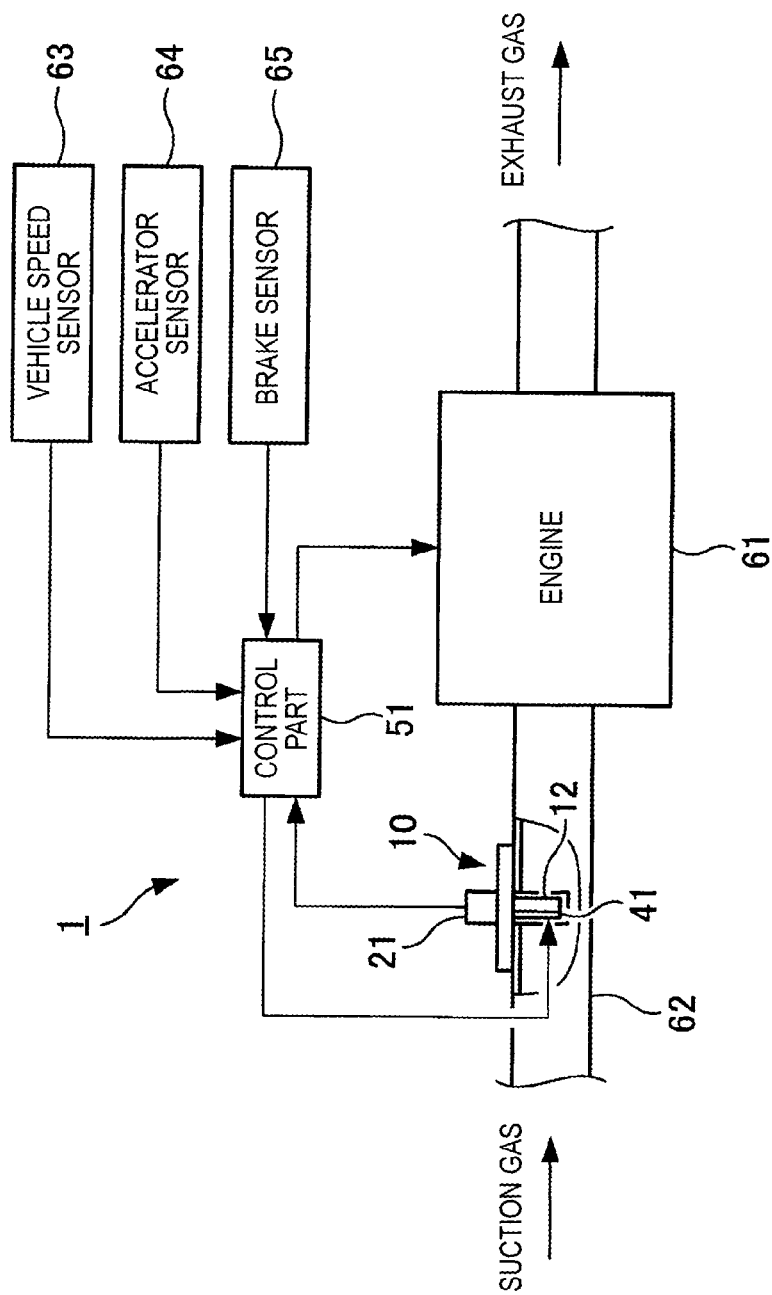
FIG. 1 is a frame-format diagram illustrating a schematic configuration of a sensor control apparatus according to an embodiment of this invention.

Various reference numbers used to identify certain features in the drawings include the following.
1 sensor control apparatus
10 oxygen sensor (gas sensor)
12 sensor element
13 housing
16 O ring (seal part)
21 base part
41 heater (heating part)
51 control part
61 engine (internal combustion engine)
62 suction pipe (pipe)
S12 determining step
S15, S16 stop control step

DETAILED DESCRIPTION OF THE PREFERRED EMBODIMENTS

The sensor control apparatus according to an embodiment of this invention will be explained with reference to FIGS. 1 to 6. However, the present invention should not be construed as being limited thereto.

FIG. 1 is a frame-format diagram illustrating the schematic configuration of a sensor control apparatus 1 according to the embodiment.

As shown in FIG. 1, the sensor control apparatus 1 according to this embodiment is applied to an engine (internal combustion engine) 61 as the power source for a vehicle such as an automobile. Concretely, the sensor control apparatus 1 performs a temperature control with respect to an oxygen sensor 10 for measuring the concentration of oxygen as the component of a particular gas contained in gas drawn into the engine 61. The sensor control apparatus 1 is mainly provided with the oxygen sensor 10, a heater (heating part) 41 and a control part 51.

Figure 2:
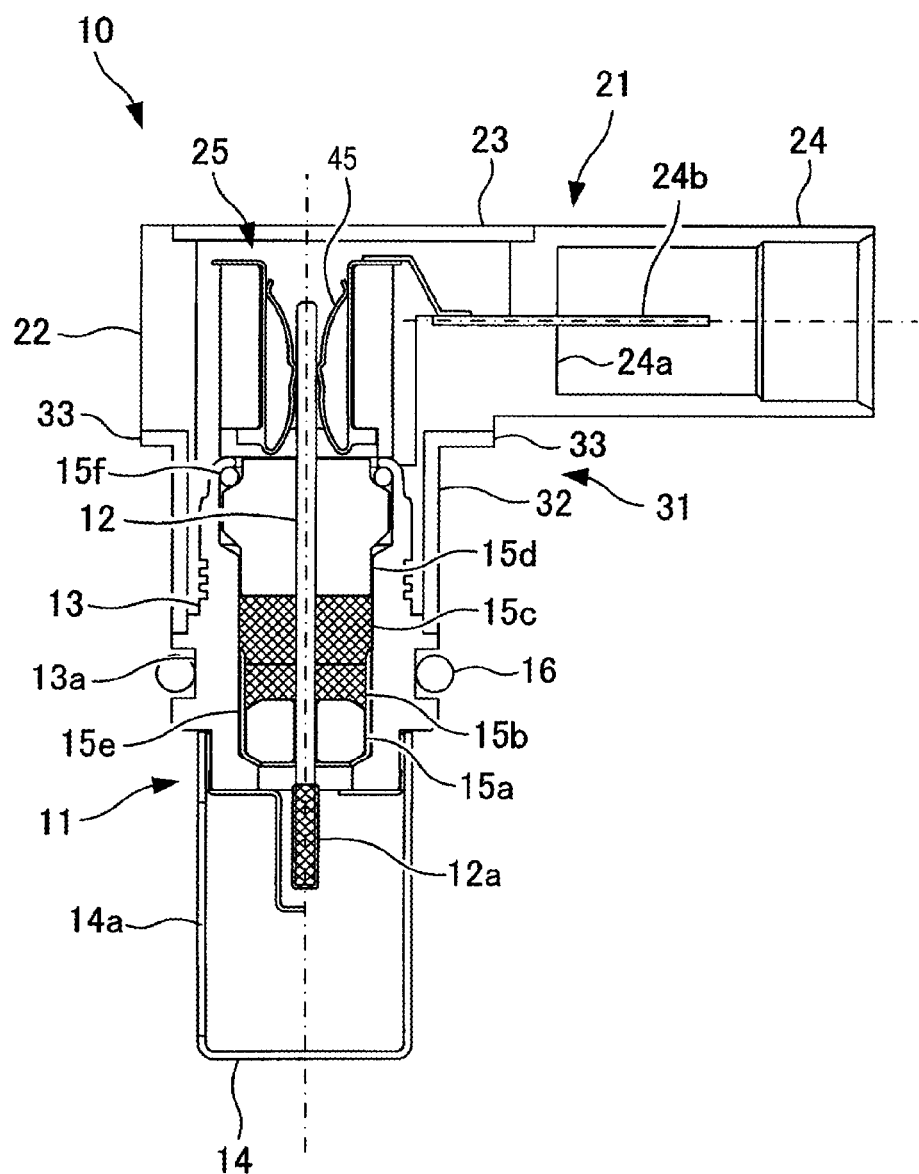
FIG. 2 is a sectional diagram illustrating the structure of an oxygen sensor of FIG. 1.

FIG. 2 is a sectional diagram illustrating the structure of the oxygen sensor 10 of FIG. 1. FIGS. 3(a)-3(d) and FIGS. 4(a)-4(d) are diagrams showing the assembly procedure of the oxygen sensor 10 for illustrating the configuration of the oxygen sensor 10 of FIG. 2.

The oxygen sensor 10 is disposed in the suction pipe (pipe) 62 of the engine 10 and measures the oxygen concentration of suction gas used for the air-fuel ratio control, etc., of the engine 61. As shown in FIG. 2, the oxygen sensor 10 is mainly constituted by an element assembly 11 containing a sensor element 12, a base part 21 and a heat sink part 31.

The element assembly 11 is configured such that almost the entirety thereof is inserted into the suction pipe 62 and the sensor element 12 for measuring the oxygen concentration of the suction gas is housed therein. As shown in FIG. 2 and FIG. 3(a), the element assembly 11 is mainly configured by the sensor element 12, a housing 13 for housing the sensor element 12 therein and which holds the sensor element 12, an external protector 14, a ceramic ring 15a, a first talc ring 15b, a second talc ring 15c, a sleeve 15d, and an O ring (seal part) 16 for holding an airtight state between the suction pipe 62 and the oxygen sensor 10.

The sensor element 12 acts as a measuring part for measuring the oxygen concentration of the suction gas flowing through the suction pipe 62. The sensor element 12 is configured by mainly laminating sequentially a pump cell, an insulation layer having a hollow measuring chamber, an electromotive cell, a reinforcement plate and the heater 41 described below.

The pump cell is formed by partially stabilized zirconia ($ZrO_2$) as an oxygen ion conducting solid electrolyte. A porous electrode mainly formed of platinum is provided on each of the major surface and the rear surface of the pump cell.

Like the pump cell, the electromotive cell is formed by partially stabilized zirconia ($ZrO_2$) as the oxygen ion conducting solid electrolyte. A porous electrode mainly formed by platinum is provided on each of the major surface and the rear surface of the electromotive cell.

One of the pair of porous electrodes provided at the pump cell and one of the pair of porous electrodes provided at the electromotive cell are disposed so as to face the measuring chamber. The electrodes disposed so as to face the measuring chamber are electrically connected to the same voltage and further coupled to a single electrode extracting part formed at the rear end side surface of the sensor element 12.

The porous electrode disposed on the opposite side of the measuring chamber in the pump cell and the porous electrode disposed on the opposite side of the measuring chamber in the electromotive cell are coupled to two electrode extracting parts formed at the rear end side surface of the sensor element 12, respectively.

The reinforcement plate is laminated on the electromotive cell so as to form a reference oxygen chamber within the porous electrode which is disposed on the opposite side of the measuring chamber in the electromotive cell while covering the porous electrode.

As described above, the insulation layer forming the measuring chamber therein is disposed between the pump cell and the electromotive cell. The measuring chamber is in communication with the external gas atmosphere, that is, the suction gas flowing within the suction pipe 62 via a porous diffusion layer separately provided within the insulation layer.

The sensor element 12 has at its tip end (lower end in FIG. 2) a detection part 12a in which a current according to the oxygen concentration flows and also has at its rear end (upper end in FIG. 2) three electrode extracting parts and two terminal parts for supplying electric power to the heater 41. The sensor element 12 is configured such that the flowing direction and magnitude of the current flowing in the oxygen pump cell is controlled by the control part 51 described below so that an electromotive force (voltage between the electrodes) generated in the electromotive cell becomes a predetermined constant value. The portion of the oxygen pump cell where the porous electrodes are disposed corresponds to the detection part 12a.

The heater 41 is laminated on the reinforcement plate and integrated with the pump cell, the electromotive cell and the reinforcement plate. The heater 41 is configured such that a heater resistance element formed by a conductive material is sandwiched by a pair of alumina sheets. The heater 41 is coupled at its one end to a DC power source (battery of 12 volts) and coupled at its the other end to a heater control circuit 53 (see FIG. 5). When the heater 14 is heated by driving the heater control circuit 53, since the temperature of each of the pump cell and the electromotive cell is increased so as to activate the same, gas detection (oxygen concentration detection) using the sensor element 12 is made possible.

The housing 13 is formed by metal, for example, stainless steel and has a cylindrical shape having a thickness that is larger than that of the external protector 14. The housing houses therein the ceramic ring 15a, the first talc ring 15b, the second talc ring 15c, the sleeve 15d, the sensor element 12, etc. The housing 13 is provided at an almost center portion of the outer peripheral surface thereof with a groove part 13a which is formed in an annular shape so as to accommodate the O ring 16 therein. The tip end side (lower side in FIG. 2) of the housing 13 is formed to have an outer diameter smaller than that of the center portion thereof. The external protector 14 is attached to this tip end side portion.

The external protector 14 is a metal member formed in a cylindrical shape having one end which is closed and which houses the detection part 12a of the sensor element 12 therein to thereby protect the detection part 12a. The external protector 14 is fixed to the housing 13 in a state such that the end portion of the tip end side of the housing 13 is inserted into the opening portion of the cylindrical shape.

A gas induction hole 14a is provided at the circumferential surface of the external protector 14. The gas induction hole 14a acts to draw the suction gas flowing through the suction pipe 62 into the external protector 14 and to draw the suction gas to the periphery of the detection part 12a of the sensor element 12. In this embodiment, the gas induction hole 14a is a through hole formed in a rectangular shape extending along the center axis direction (upper and lower direction in FIG. 2) of the cylindrical shape of the external protector 14.

The ceramic ring 15a is a member formed in a cylindrical shape made from alumina ($Al_2O_3$). The sensor element 12 is inserted into the ceramic ring 15a. Each of the first talc ring 15b and the second talc ring 15c is a member which is formed by compressing and solidifying talc powder into a cylindrical shape. The sensor element 12 is inserted into these first and second talc rings.

The ceramic ring 15a, the first talc ring 15b and the second talc ring 15c are disposed in this order toward the rear end of the sensor element 12 from the tip end thereof. Further, the entirety of each of the ceramic ring 15a and the first talc ring 15b and the lower end of the second talc ring 15c are housed within a metal cup 15e which one end is closed and which is formed in a cylindrical shape. The metal cup 15e is disposed between the inner peripheral surface of the housing 13 and the outer peripheral surface of each of the ceramic ring 15a and the first talc ring 15b. A through hole for passing the sensor element 12 therethrough is formed at the closed end portion of the metal cup 15e.

The sleeve 15d is a member which is disposed on the rear end side of the second talc ring 15c and formed in a cylindrical shape. The sleeve 15d acts to press the ceramic ring 15a, the first talc ring 15b and the second talc ring 15c toward the tip end of the sensor element 12 together with the housing 13. A packing 15f of an annular shape is disposed between the rear end (upper end in FIG. 2) of the sleeve 15d and the housing 13. The packing 15f hermetically closes a space between the sleeve 15d and the housing 13.

The O ring 16 is a member formed in a ring shape and is made of a resin such as a rubber having elasticity. The O ring is formed in a circular shape in its section. The O ring 16 is disposed in the groove part 13a of the housing 13. The inner peripheral side portion of the O ring 16 contacts the bottom surface of the groove part 13a. The outer peripheral side portion of the O ring 16 contacts the inner peripheral surface of a through hole which is provided at the suction pipe 62 and in which the oxygen sensor 10 is inserted.

When the O ring 16 for closing a gap between the housing and the suction pipe 62 is provided at the housing 13 in this manner, the suction gas can be prevented from leaking to the outside from the inner portion of the suction pipe 62. Even when the O ring 16 is formed by the resin having elasticity, since a control in the stop state is performed by the control part 51, the O ring 16 is unlikely to suffer damage due to softening by a temperature increase.

Figure 3:
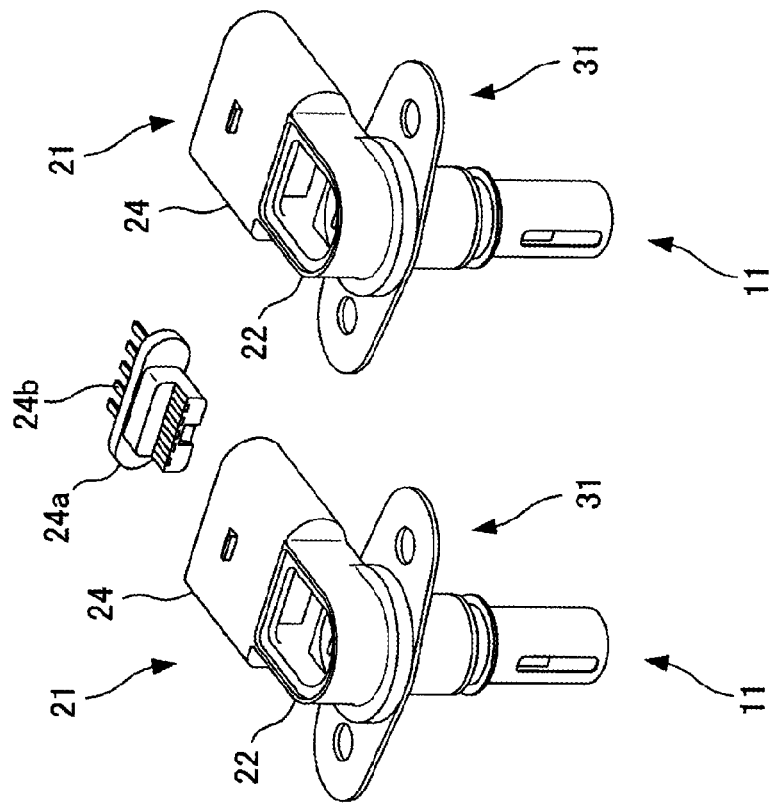
FIGS. 3(a)-3(d) are diagrams showing a first half of the assembling process of the oxygen sensor illustrating the configuration of the oxygen sensor of FIG. 1.

The base part 21 is disposed outside of the suction pipe 62 and is formed of a resin having formability as compared with other members. As shown in FIG. 2 and FIGS. 3(*c*) and (*d*), the base part 21 is mainly provided with a main body 22, a lid part 23 and a connector part 24. In this embodiment, the base part 21 is formed of polyphenylene sulfide.

The main body 22 is formed by the insert molding at a gap between the housing 13 and the heat sink part 31, and has a pillar shaped space for housing a separator 25 therein. The lid part 23 is a plate shaped member for closing the pillar shaped space provided at the main body 22. The lid part 23 hermetically closes this space in a state such that the separator 25 is housed within this space.

As shown in FIG. 2, the separator 25 is formed of a ceramic having insulation properties and is configured in a cylindrical shape. Five terminal members 45 for electrically connecting to the sensor element 12 are disposed within the separator 25, and the rear end portion of the base part 21 side of the sensor element 12 is also inserted into the separator 25. When the rear end portion of the sensor element 12 is inserted into the separator 25, the five electrode terminal parts of the sensor element 12 contact the five terminal members 45, respectively.

The connector part 24 constituting the base part 21 is configured such that a terminal body 24a provided with five connector terminals 24b disposed in a line with a space therebetween is provided within a cylindrical portion which extends in a direction crossing with respect to a direction (upper and lower direction in FIG. 2) where the sensor element 12 extends, more preferably, a direction (left and right directions in FIG. 2) orthogonal thereto. The connector terminals 24b are coupled to the terminal members 45, respectively, whereby the electrical coupling between the sensor element 12 and the control part 51 can be performed via the connector part 24.

As shown in FIG. 2, the heat sink part 31 is a heat dissipation portion disposed between the element assembly 11 and the base part 21 and is used at the time of attaching the oxygen sensor 10 to the suction pipe 62. The heat sink part 31 is formed of a metal such as aluminum, aluminum alloy or stainless steel, that is, a material having a higher thermal conductivity than that of resin. As shown in FIG. 2 and FIG. 3(*b*), the heat sink part 31 is mainly provided with a casing part 32 and a flange part 33.

As shown in FIG. 2 and FIG. 3(*b*), the casing part 32 is a member formed in a cylindrical shape and the element assembly 11 is inserted therein. The tip end side (lower side in FIG. 2) of the casing part 32 is fixed to the housing 13 such that the entire periphery thereof is subjected to laser welding.

The flange part 33 is configured by a pair of sheet members which extend to opposite directions toward the outside in the radial direction of the cylindrical casing part 32 from the end portion on the base part 21 side (upper side in FIG. 3(*b*)) of the casing part 32. The flange part 33 is provided with insertion holes 34 into each of which a fixing bolt, etc., used for fixing the oxygen sensor 10 to the suction pipe 62 is inserted.

Figure 5:
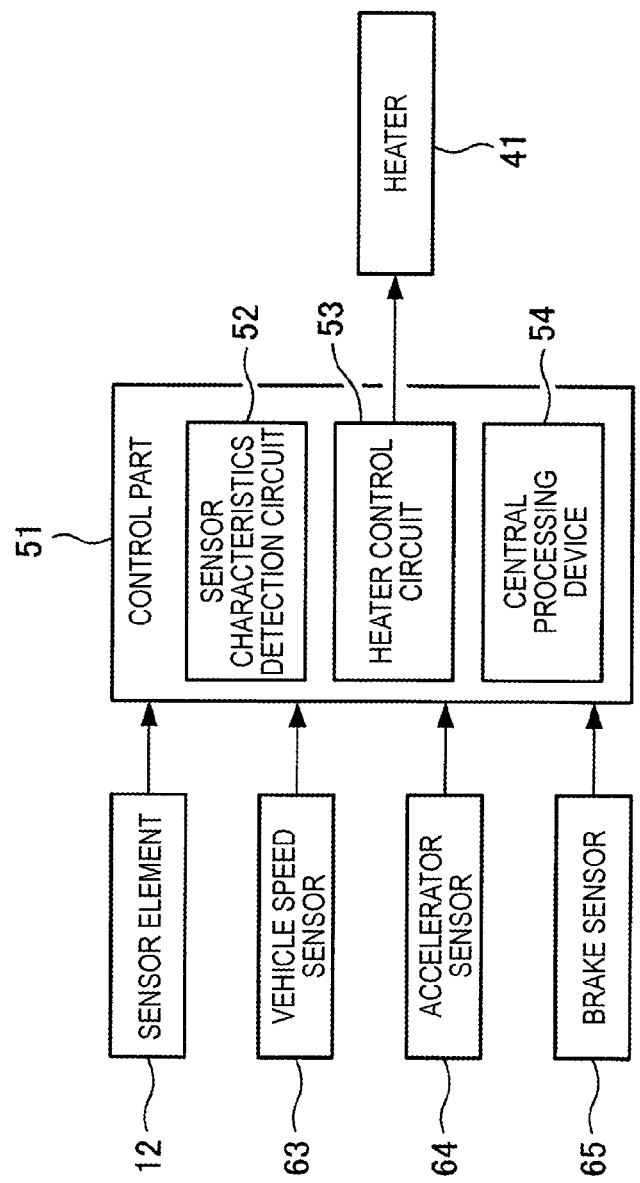
FIG. 5 is a block diagram illustrating the input/output of a control part of FIG. 1.

FIG. 5 is a block diagram illustrating the input/output of the control part 51 in FIG. 1.

The control part 51 adjusts electrical energy supplied to the heater 41 and also performs control functions such as the idling stop control with respect to the engine 61 based on input from various sensors. As shown in FIG. 5, the control part 51 receives measurement signals from the various kinds of sensors such as the sensor element 12, a vehicle speed sensor 63 for measuring the running speed of the vehicle, an accelerator sensor 64 for measuring the depression amount of an accelerator pedal and a brake sensor 65 for measuring the depression amount of a brake pedal. The control part 51 outputs a control signal for the heater 41. The control part 51 is mainly provided with a sensor characteristics detection circuit 52, the heater control circuit 53 and a central processing device 54.

The sensor characteristics detection circuit 52 is electrically coupled to the three electrode terminal parts of the sensor element 12 to be coupled to the pump cell and the porous electrode of the electromotive cell. The sensor characteristics detection circuit 52 includes (i) a circuit part for supplying a small current into the electromotive cell such that the porous electrode located on the reinforcement plate side of the electromotive cell acts as a reference oxygen electrode, (ii) a circuit part for controlling the direction and magnitude of the current flowing into the pump cell such that the electromotive force (voltage between electrodes) generated at the electromotive cell becomes a predetermined voltage, and (iii) a circuit part for converting the current flowing into the pump cell into a voltage to thereby detect the voltage as a gas detection signal. The sensor characteristics detection circuit 52 further includes a circuit part for periodically supplying an impedance detection current into the sensor element 12 (concretely, an electromotive cell) to thereby detect an instantaneous voltage changing amount as an element impedance signal. The gas detection signal and the element impedance signal detected by the sensor characteristics detection circuit 52 are outputted to the central processing device 54. The gas detection signal is a signal which value changes linearly in accordance with the oxygen concentration detected by the sensor element 12 (pump cell).

The heater control circuit 53 controls the electrical energy supplied to the heater 41 based on the control signal inputted from the central processing device 54. To be concrete, the heater control circuit controls the electrical energy (power supply amount) supplied to the heater 41 in a manner such that the turning-on/off control of a switching element (FET, for example) provided at the heater control circuit 53 and electrically coupled to the heater 41 is subjected to a known PWM (pulse width modulation) current conduction control based on the control signal from the central processing device 54.

The central processing device 54 is mainly configured by a microcomputer which includes a CPU, a RAM, a ROM, an I/O interface, etc. The central processing device 54 performs various kinds of control processing by using information inputted from the various kinds of sensors.

For example, the central processing device 54 performs a temperature detection processing for calculating the temperature of the sensor element 12 by using the element impedance signal inputted from the sensor characteristics detection circuit 52, and further performs a heater control processing for controlling the electrical energy supplied to the heater 41 necessary for setting the temperature of the sensor element 12 to a target temperature, for example. Further, the central processing device 54 performs a gas concentration detection processing for calculating the oxygen density of the suction gas based on the gas detection signal inputted from the sensor characteristics detection circuit 52.

Figure 4:
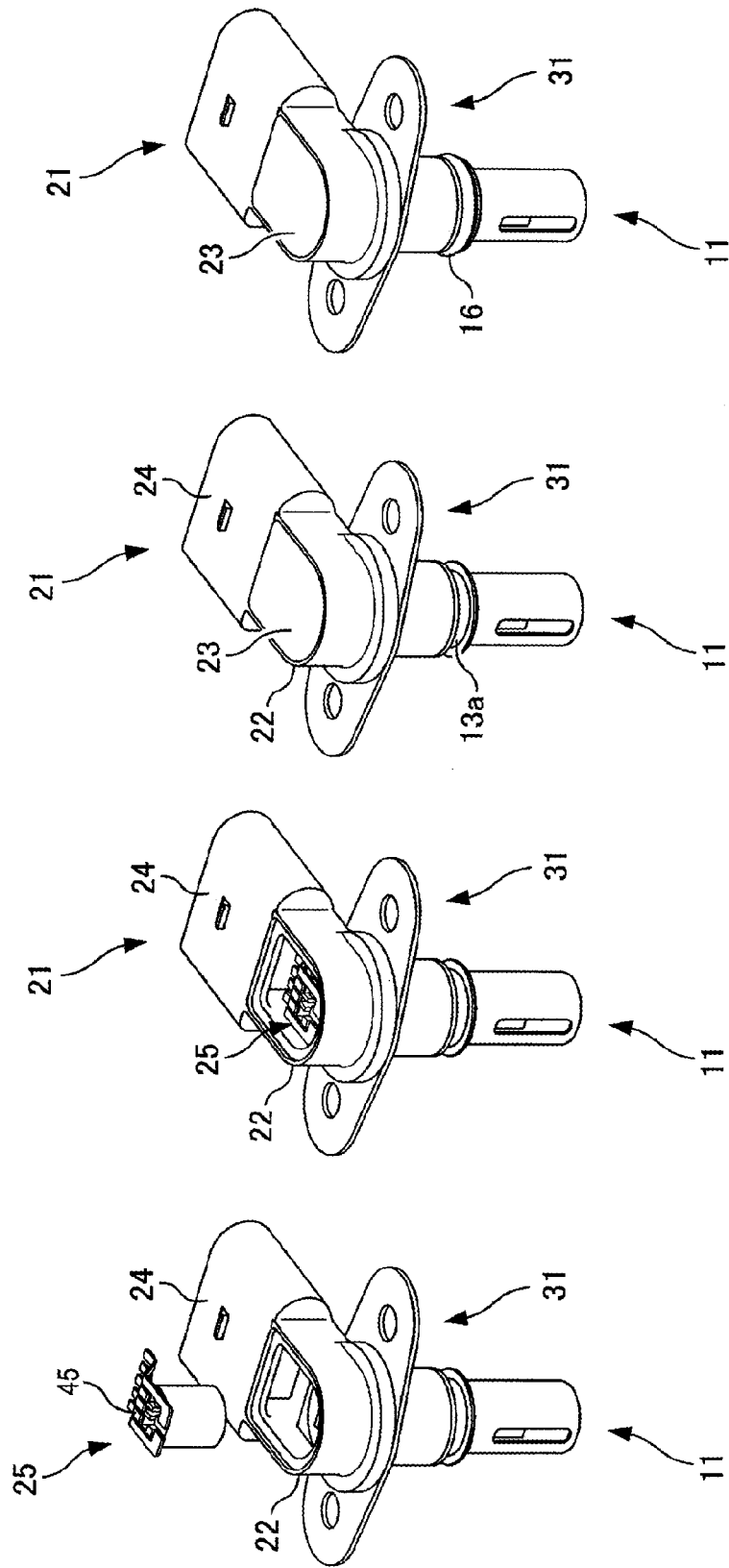
FIGS. 4(a)-4(d) are diagrams showing a second half of the assembling process of the oxygen sensor illustrating the configuration of the oxygen sensor of FIG. 1.

The assembly procedure of the oxygen sensor 10 will be explained briefly with reference to FIGS. 3 and 4. First, the element assembly 11 is prepared as shown in FIG. 3(a). Then, as shown in FIG. 3(b), the heat sink part 31 is fixed to the element assembly 11 thus prepared by laser welding. Thereafter, the cylindrical portions of the main body 22 of the base part 21 and the connector part 24 are formed by inserting molding at the gap between the housing 13 and the heat sink part 31. The terminal body 24a is inserted into the cylindrical portion of the connector part 24, whereby the oxygen sensor 10 is placed in a state shown in FIG. 3(d).

Thereafter, as shown in FIGS. 4(a) and (b), the separator 25 attached with the terminal member 45 is attached to the base part 21, and the rear end portion of the sensor element 12 is inserted into the separator 25. Then, as shown in FIG. 4(c), the space where the separator 25 is disposed is closed by the lid part 23. Finally, as shown in FIG. 4(d), the O ring 16 is attached into the groove part 13a of the housing 13 to thereby complete assembly of the oxygen sensor 10.

Figure 6:
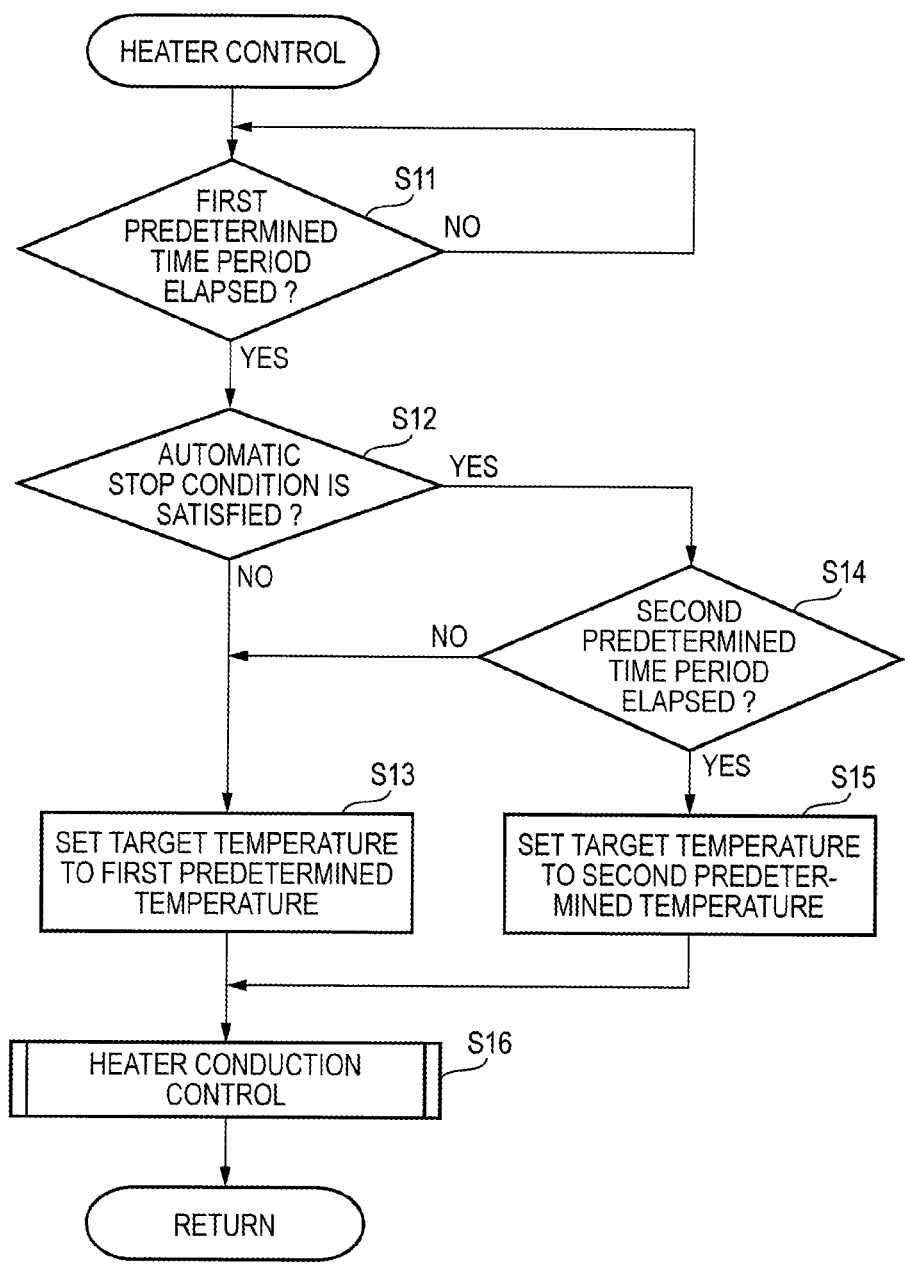
FIG. 6 is a flowchart illustrating the conduction of a heater including a case where an internal combustion engine is stopped due to an idling stop control.

Next, an explanation will be made as to control of the sensor control apparatus 1 thus configured. First, the explanation will be made as to temperature control of the sensor element 12 by the sensor control apparatus 1 in the case where the engine 61 is driven. Thereafter, the explanation will be made with reference to FIG. 6 as to characteristic control of this embodiment in the case where the engine 61 is stopped due to the idling stop control. FIG. 6 is a flowchart illustrating the control processing in the sensor control apparatus 1 of this embodiment in the case where the engine 61 is stopped due to the idling stop control.

In the case where the engine 61 is driven and the oxygen concentration contained in the suction gas flowing through the suction pipe 62 is measured by the oxygen sensor 10, the temperature of the sensor element 12 is controlled to be a so-called activating temperature by the sensor control apparatus 1.

The activating temperature is a temperature necessary for the sensor element 12 to measure the oxygen concentration contained in the suction gas. The activating temperature differs depending on material constituting the sensor element 12. For example, in the case of the sensor element 12 for measuring the oxygen concentration made of zirconia ($ZrO_2$), the activating temperature is a temperature necessary for zirconia to act as oxygen ion conductor.

Concretely, the temperature of the sensor element 12 is calculated by the sensor characteristics detection circuit 52 and the central processing device 54 of the control part 51. This calculation is executed by a processing different from that of the flowchart shown in FIG. 6. The sensor characteristics detection circuit 52 detects the element impedance signal, which relates to an element resistance value, periodically outputted from the sensor element 12 and outputs the element impedance signal thus detected to the central processing device 54. The central processing device 54 performs a calculation for estimating the temperature of the sensor element 12 using the element impedance signal thus inputted.

The value (voltage value, for example) of the element impedance signal changes according to the temperature of the sensor element 12. Thus, when an arithmetic expression for obtaining the temperature of the sensor element 12 from the value of the element impedance signal is stored in the storage device such as the ROM of the central processing device 54 in advance, the temperature of the sensor element 12 can be obtained based on the arithmetic expression. Alternatively, a table describing the correspondence between the values of the element impedance signal and the temperature values of the sensor element 12 may be stored in advance into the ROM etc., and the temperature of the sensor element 12 may be obtained with reference to the table.

When the temperature of the sensor element 12 is obtained, the central processing device 54 compares the temperature of the sensor element 12 thus obtained with the target temperature. The target temperature is a target value of the temperature of the sensor element 12 to be controlled by the central processing device 54 and corresponds to a target of the element resistance value of the sensor element 21. In a state where the engine 61 is driven, the target temperature is set to a first predetermined temperature (830° C., for example) as the activating temperature.

When the temperature of the sensor element 12 thus obtained is lower than the target temperature, the central processing device 54 generates a control signal for increasing the temperature of the sensor element 12. That is, the central processing device generates the control signal for increasing the electrical energy supplied to the heater 41 and outputs this control signal to the heater control circuit 53. Since an amount of heat generated from the heater 41 increases due to the increase of the electrical energy that is supplied, the temperature of the sensor element 12 increases.

In contrast, when the temperature of the sensor element 12 thus obtained is higher than the target temperature, the central processing device 54 generates a control signal for reducing the temperature of the sensor element 12. That is, the central processing device generates the control signal for reducing the electrical energy supplied to the heater 41 and outputs this control signal to the heater control circuit 53. An amount of heat generated from the heater 41 is reduced due to reduction of the electrical energy that is supplied. In the sensor element 12, since an amount of heat drawn by the suction gas, etc., becomes larger than an amount of heat supplied from the heater 41, the temperature of the sensor element 12 is reduced.

The control part 51 performs the control repeatedly to thereby control the temperature of the sensor element 12 so as to be near the target temperature, that is, the activating temperature. Thus, the oxygen concentration of the suction gas can be measured stably.

Next, control in the case where the engine 61 is stopped due to the idling stop control will be explained. When the engine 61 is stopped, the central processing device 54 of the control part 51 compares an elapsed time after the stop of the engine with a first predetermined time period (3 seconds, for example) (S11). As a method of detecting the stop of the engine 61, one of known methods may be employed such as a method of detecting information such as the rotation speed of the engine or the vehicle speed and a method of detecting the supply/non-supply of electric power to ignition plugs, for example, and the method is not limited to a particular one.

When the elapsed time is shorter than the first predetermined time period (in the case of No), the process returns to S11 and the comparison between the elapsed time and the first predetermined time period is repeated.

In contrast, when the elapsed time is equal to or longer than the first predetermined time period (in the case of Yes), the central processing device 54 determines whether or not the engine 61 is stopped due to the satisfaction of a predetermined automatic stop condition, that is, due to the idling stop control (S12: determining step).

The automatic stop condition may be a condition, for example, which satisfies all of following facts that (1) the vehicle speed measured by the vehicle speed sensor 63 is 0 km/h, (2) the depression amount of the acceleration pedal measured by the accelerator sensor 64 is 0 (acceleration pedal is not depressed), and (3) depression of the brake pedal is detected by the brake sensor 65. In other words, the stop of the engine 61 due to the idling stop control means the stop of the engine executed irrespective of the intension of a driver when all the aforesaid conditions (1) to (3) are satisfied.

The aforesaid conditions raised as the automatic stop condition are examples, and other conditions may be used for the automatic stop condition. Further, the number of the conditions used for the automatic stop condition may be larger or smaller than three.

When it is determined that the predetermined automatic stop condition is not satisfied in S12 (in the case of No), the central processing device 54 sets the target temperature stored in advance to a first predetermined temperature (S13). On the other hand, when it is determined that the predetermined automatic stop condition is satisfied in S12 (in the case of Yes), the elapsed time after the determination that the predetermined automatic stop condition is satisfied is compared with a second predetermined time period (15 seconds, for example) (S14). When the elapsed time is shorter than the second predetermined time period (in the case of No), the central processing device 54 performs the processing of S13. On the other hand, when the elapsed time is equal to or longer than the second predetermined time period (in the case of Yes), the central processing device 54 sets the target temperature stored in advance to a second predetermined temperature (S15).

The second predetermined time period is preferably a time period during which the temperature of the base part 21 is maintained to a temperature lower than the shape holding temperature of the resin in the case where the control for holding the temperature of the sensor element 12 to the activating temperature by using the heater 41 is continued, after the predetermined automatic stop condition is satisfied.

The second predetermined temperature is a temperature which is equal to or lower than the shape holding temperature of the resin forming the base part 21 and lower than the first predetermined temperature, that is, the activating temperature of the sensor element 12, and further, at least equal to or higher than 100° C.

In the case where the heater 41 is continuously supplied with the electric power to thereby set the temperature of the sensor element 12 to a temperature equal to or higher than 100° C. and lower than the activating temperature, when the driving of the engine 61 having been stopped by the idling stop control is started again, the temperature of the sensor element 12 can be quickly increased (restored) to the activating temperature within a time period not adversely affecting the control (air-fuel ratio control, for example) of the engine 61.

Further, even when the engine 61 stops by the idling stop control and then the control for reducing the temperature of the sensor element 12 is performed, the sensor element 12 can be prevented from being adhered with water (water droplets). That is, since the temperature of the sensor element 12 is kept at 100° C. or higher, the water evaporates and does not adhere to the sensor element 12. Thus, when the engine 61 having been stopped by the idling stop control is driven again and the temperature of the sensor element 12 is increased so as to reach the activating temperature, the following phenomenon can be suppressed. That is, the sensor element 12 has a portion which is not adhered with water droplets and hence the heating process thereof is promoted, and also has another portion which is adhered with water droplets and hence the heating process thereof is delayed. Thus, the sensor element 12 may be damaged by thermal shock caused by an abrupt temperature increase of the another portion when the water droplets adhered thereto evaporate.

The shape holding temperature of the resin is a temperature that can maintain the shape of the base part 21 formed by a resin so as to be able to attain the function of the base part 21. For example, the shape holding temperature of the resin is a temperature determined based on a deflection temperature under load of the resin to be used or a melting point, etc., thereof as a parameter. In this embodiment, since polyphenylene sulfide is used, the parameter is the deflection temperature under load.

The second predetermined temperature is preferably set to a temperature lower than the activating temperature and equal to or higher than 300° C. More preferably, the second predetermined temperature is set to a temperature lower than the activating temperature and equal to or higher than 600° C.

When the temperature of the sensor element 12 is set to be equal to or higher than 300° C. and lower than the activating temperature, the sensor element 12 can be prevented from being adhered with oil. In other words, since the temperature of the sensor element 12 is kept at 300° C. or higher, the oil is evaporated and does not adhere to the sensor element 12 as soon as the oil contacts the sensor element 12. Thus, the adherence of soot due to the adhering of oil to the sensor element 12 can be suppressed.

Further, when the temperature of the sensor element 12 is set to be equal to or higher than 600° C. and lower than the activating temperature, since the temperature of the sensor element 12 is kept at 600° C. or higher, even if soot adheres to the sensor element 12, the soot thus adhered is burnt and hence does not remain on the sensor element 12. Thus, a phenomenon that the output according to the concentration of the particular gas is influenced by the conductive soot attached to and remaining on the sensor element 12 can be suppressed. In this embodiment, the second predetermined temperature is set to 600° C., as an example.

Further, the central processing device 54 may set an element impedance (Rpvs) of the sensor element 12 corresponding to the first predetermined temperature or the second predetermined temperature, as the value set as the target temperature.

When the target temperature is set in S13 or S15, the central processing device 54 starts a heater conduction control for controlling the voltage and current supplied to the heater 41 to thereby control the temperature of the sensor element 12 to the target temperature (S16). The processes of S15 and S16 correspond to the control step in the stop state of the invention.

In the heater conduction control in the case where the target temperature is set to the first predetermined temperature, a control similar to the heater conduction control in the case where the engine 61 is driven is performed.

On the other hand, in the heater conduction control in the case where the target temperature is set to the second predetermined temperature, the voltage and current supplied to the heater 41 is controlled so that an amount of heat generated from the heater 41 is reduced (control in the stop state is performed).

According to the aforesaid configuration, when the engine 61 stops in the manner of satisfying the automatic stop condition, in other words, when the engine stops by the idling stop control, the control part 51 performs the control in the stop state for reducing at least one of the voltage and current supplied to the heater 41. An amount of the reduction of at least one of the voltage and current is set to an amount which can reduce an amount of heat transmitted to the base part 21 from the sensor element 12 to thereby set the temperature of the base part 21 to a value equal to or lower than the shape holding temperature of the resin, in the case where the engine 61 stops (namely, when the flow of the suction gas flowing through the suction pipe 62 stops and an amount of heat drawn from the sensor element 12 by the suction gas is reduced).

Further, in this embodiment, the control is switched into the control in the stop state (S15) upon the lapse of the second predetermined time period (Yes in S14) after it is determined that the engine 61 is stopped due to satisfaction of the predetermined automatic stop condition (Yes in S12). According to such a process, when the engine 61 is driven again immediately after it is determined that the engine is stopped due to the satisfaction of the predetermined automatic stop condition, the temperature of the sensor element 12 is maintained at the activating temperature without being reduced. Thus, the control (air-fuel ratio control, for example) of the engine 61 can be continued favorably.

Figure 7:
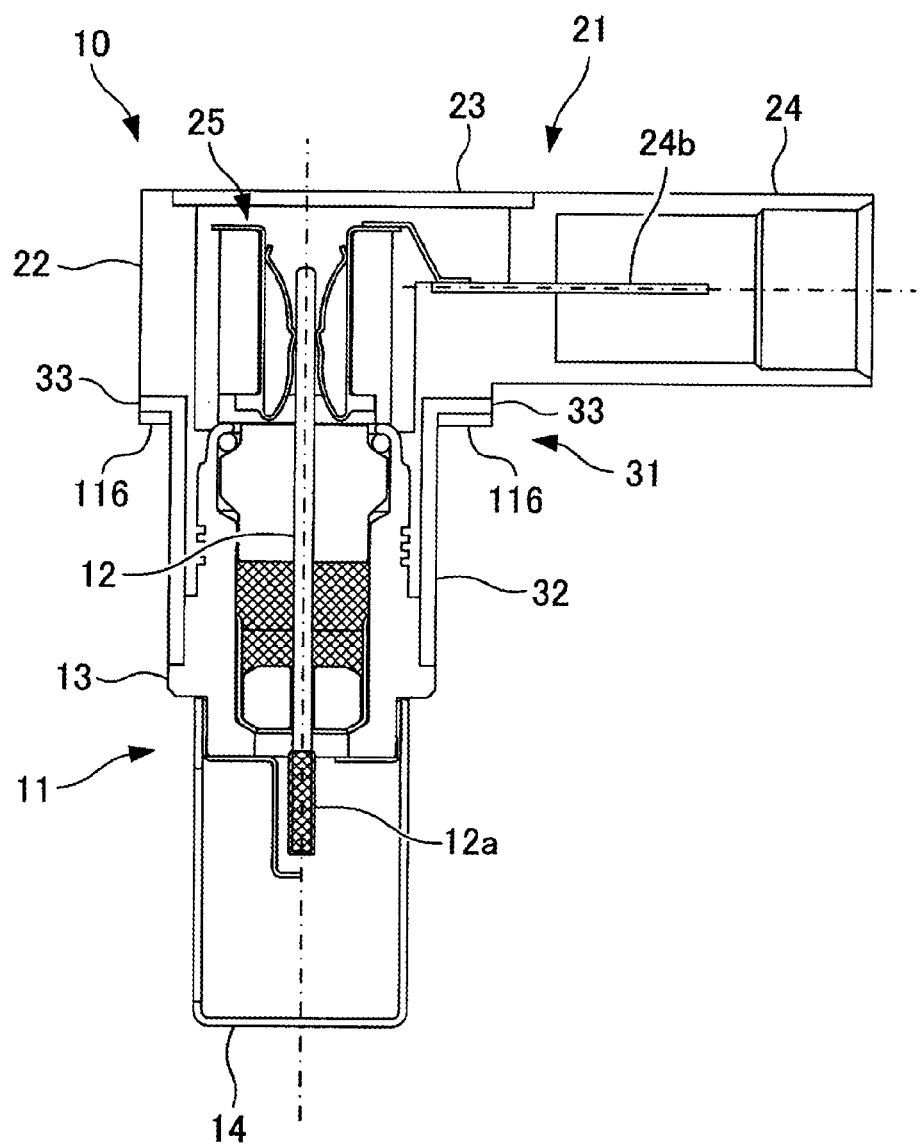
FIG. 7 is a sectional diagram illustrating the structure of another embodiment of the oxygen sensor 10 shown in FIG. 2.

FIG. 7 is a sectional diagram illustrating the structure of another embodiment of the oxygen sensor 10 shown in FIG. 2. Like the aforesaid embodiment, the oxygen sensor 10 may be provided with the O ring 16. Alternatively, in place of the O ring 16, as shown in FIG. 7, a seal member 116 made of metal and formed in a sheet shape may be disposed on the surface contacting with the suction pipe 62 of the flange part 33 of the heat sink part 31. However, the kind and disposing position of the seal member is not particularly limited.

In the aforesaid embodiment, in the flowchart shown in FIG. 6, the process (S15) of setting the target temperature to the second predetermined temperature is performed when it is determined that the automatic stop condition is satisfied (Yes in S12) and when the second predetermined time period elapses (Yes in S14). However, the process of S15 may be performed immediately after it is determined that the automatic stop condition is satisfied (Yes in S12) without performing the process of S14.

Further, in the aforesaid embodiment, the second predetermined temperature is set as the target temperature of the sensor element 12 in the process of S15 in the flowchart shown in FIG. 6. However, in place of this process, a process of controlling the electrical energy supplied to the heater 41 to a constant amount (a 3 volt constant control, for example) within a range that the temperature of the base part 21 is made equal to or lower than the shape holding temperature of the resin may be executed as the control in the stop state for the heater 41. In this case, the control for setting the temperature of the base part 21 so as to be equal to or lower than the shape holding temperature of the resin can be realized by the simple control of setting the electrical energy supplied to the heater 41 to a constant amount.

Also in the case of performing the process of controlling the electrical energy supplied to the heater 41 to a constant amount as the control in the stop state, it is favorable to control the electrical energy supplied to the heater so as to set the temperature of the sensor element 12 to be lower than the activating temperature and equal to or higher than 100° C., preferably 300° C., and more preferably 600° C.

The invention has been described in detail by reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-055602, filed Mar. 14, 2011, the disclosure of which is incorporated herein by reference in its entirety.

What is claimed is:

1. A sensor control apparatus comprising:
   a gas sensor which comprises:
      a sensor element for measuring a concentration of a particular gas component contained in a gas flowing within a pipe disposed in an internal combustion engine,
      a housing which houses the sensor element therein and is inserted into the pipe, and
      a base part which is formed of a resin, attached to the housing and disposed on an outer side of the pipe;
   a heating part which increases a temperature of the sensor element; and
   a control part which adjusts at least one of voltage and current supplied to the heating part to maintain the temperature of the sensor element at an activating temperature, wherein
   the control part determines whether or not, when the internal combustion engine having been driven is stopped, the internal combustion engine is stopped in a manner satisfying a predetermined automatic stop condition, and wherein
   when it is determined that the internal combustion engine is stopped in the manner satisfying the predetermined automatic stop condition, the control part switches from a control for maintaining the temperature of the sensor element at the activating temperature to a control in a stop state for reducing at least one of the voltage and current supplied to the heating part to thereby set a temperature of the base part to a value equal to or lower than a shape holding temperature of the resin.

2. The sensor control apparatus as claimed in claim 1, wherein the control part selectively supplies electric power and stops supply of electric power to the heating part at a time of the control in a stop state, and continuously supplies electric power to the heating part at a time of performing the control in a stop state.

3. The sensor control apparatus as claimed in claim 1, wherein at the time of performing the control in a stop state, the control part adjusts at least one of the voltage and current supplied to the heating part so that the temperature of the sensor element becomes 100° C. or higher and lower than the activating temperature.

4. The sensor control apparatus as claimed in claim 1, wherein at the time of performing the control in a stop state, the control part adjusts at least one of the voltage and current supplied to the heating part so that the temperature of the sensor element becomes 300° C. or higher and lower than the activating temperature.

5. The sensor control apparatus as claimed in claim 1, wherein at the time of performing the control in a stop state, the control part adjusts at least one of the voltage and current supplied to the heating part so that the temperature of the sensor element becomes 600° C. or higher and lower than the activating temperature.

6. The sensor control apparatus as claimed in claim 1, wherein the control part switches to control in a stop state upon lapse of a predetermined time period after determining that the internal combustion engine is stopped due to satisfaction of the predetermined automatic stop condition.

7. The sensor control apparatus as claimed in claim 1, wherein the control part controls electric energy supplied to the heating part so as to be constant when the control in a stop state.

8. The sensor control apparatus as claimed in claim 1, wherein
while the internal combustion engine is driven, the control part adjusts at least one of the voltage and current supplied to the heating part so as to attain an element resistance value of the sensor element corresponding to the activating temperature, and wherein
at the time of performing the control in a stop state, the control part adjusts at least one of the voltage and current supplied to the heating part so as to attain an element resistance value corresponding to a temperature of the sensor element at which a temperature of the base part is equal to or lower than the shape holding temperature of the resin.

9. The sensor control apparatus as claimed in claim 1, wherein the housing is provided with a seal part which closes a gap between the housing and the pipe to thereby prevent the gas from flowing outside of the pipe.

10. A sensor control method for holding a temperature of a sensor element to an activating temperature using a heating part for heating the sensor element, in a gas sensor which comprises the sensor element for measuring a concentration of a particular gas component contained in a gas flowing within a pipe disposed in an internal combustion engine, a housing which houses the sensor element therein and is inserted into the pipe, and a base part which is formed of a resin, attached to the housing and disposed on an outer side of the pipe, the method comprising
a determining step of determining whether or not, when the internal combustion engine having been driven is stopped, the internal combustion engine is stopped in a manner satisfying a predetermined automatic stop condition; and
when it is determined that the internal combustion engine is stopped in the manner satisfying the predetermined automatic stop condition, a control step of stopping a control for maintaining the temperature of the sensor element at the activating temperature and starting a control in a stop state for reducing at least one of voltage and current supplied to the heating part to thereby set a temperature of the base part to a value equal to or lower than a shape holding temperature of the resin.

\* \* \* \* \*